United States Patent [19]

Imuta et al.

[11] Patent Number: 5,175,313
[45] Date of Patent: Dec. 29, 1992

[54] PROCESS FOR PREPARING DIHYDROFURANONE DERIVATIVES

[75] Inventors: Junichi Imuta; Aiichiro Ori; Noriaki Kihara, all of Yamaguchi, Japan

[73] Assignee: Mitsui Petrochemical Industries, Ltd., Tokyo, Japan

[21] Appl. No.: 695,323

[22] Filed: May 3, 1991

[30] Foreign Application Priority Data

May 7, 1990 [JP] Japan .................................. 2-115792

[51] Int. Cl.$^5$ .......................................... C07D 307/28
[52] U.S. Cl. ........................... 549/321; 549/323
[58] Field of Search ........................................ 549/321

[56] References Cited

U.S. PATENT DOCUMENTS

| | | | |
|---|---|---|---|
| 4,508,731 | 4/1985 | Reibli et al. | 549/321 |
| 4,564,629 | 1/1986 | Kunz et al. | 549/321 |
| 4,876,359 | 10/1989 | Hasegawa et al. | 549/321 |

FOREIGN PATENT DOCUMENTS 0181588 5/1986 European Pat. Off. .
0014673 2/1975 Japan .

OTHER PUBLICATIONS

DeGraw, Tetrahedron, 28, 967–972 (1972).
J. March, "Advanced Organic Chemistry", 3rd Ed., pp. 411–415 (1985).
W. Walter "Beyer/Water,-Lehrbuch der Organischen Chemie", pp. 307–308 (1984).

*Primary Examiner*—C. Warren Ivy
*Assistant Examiner*—Amelia A. Owens
*Attorney, Agent, or Firm*—Birch, Stewart, Kolasch & Birch

[57] ABSTRACT

The present invention provides a process for preparing dihydrofuranone derivative of the formula (I):

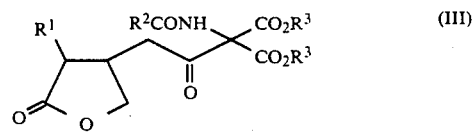

wherein $R^1$ and $R^3$ are individually lower alkyl, and $R^2$ is hydrogen or lower alkyl, by reacting a dihydrofuranone derivative of the formula(I):

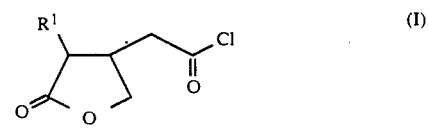

wherein $R^1$ is as defined above, with a malonic acid derivative of the formula (II):

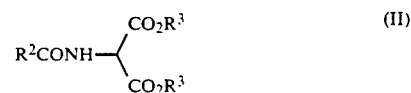

wherein $R^2$ and $R^3$ are as defined above, in the presence of an alkalimetal alkoxide and/or an alkalimetal hydroxide.

2 Claims, No Drawings

PROCESS FOR PREPARING DIHYDROFURANONE DERIVATIVES

INDUSTRIAL APPLICABILITY

The present invention relates to an industrially advantageous process for preparing a dihydrofuranone derivative of the formula (III):

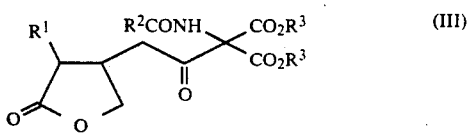

wherein $R^1$ and $R^3$ are individually lower alkyl, and $R^2$ is hydrogen or lower alkyl, which is useful as an intermediate for the synthesis of pilocarpine and analogues thereof. Pilocarpine is useful for the treatment of glaucoma.

According to the invention, the compound of the formula (III) can be prepared by reacting dihydrofuranone derivative of the formula (I):

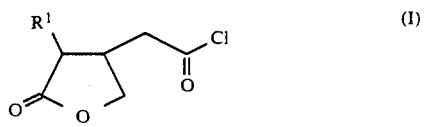

wherein $R^1$ is as defined above, with a malonic acid derivative of the formula (II):

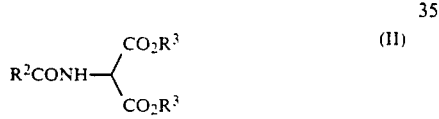

wherein $R^2$ and $R^3$ are as defined above, in the presence of a specific base.

PRIOR ART

With respect to the dihydrofurnanone derivative of the formula (I) and the malonic acid derivative of the formula (II) used as starting materials in the present invention, and to the product dihydrofuranone derivative of the formula (III), those compounds in which $R^1$ is ethyl, $R^2$ is methyl and $R^3$ is t-butyl have been disclosed in Tetrahedron 28: 967 (1972). In this reference, also the method of preparing dihydrofurnanone derivative of the formula (III) by reacting a dihydrofuranone derivative (I) with a malonic acid derivative (II) in the presence of sodium hydride has been described.

However, such a method has problems and is industrially disadvantageous, because of the inflammability of the sodium hydride used and the possibility of explosion of hydrogen gas generated during the reaction.

Problems to be solved by the Invention

An object of the invention is to provide an industrially advantageous process for preparing dihydrofuranone derivative of the formula (III) by reacting a dihydrofuranone derivative (I) with a malonic acid derivative (II) in high yield and without fear of explosion and fire.

Means for Solving the Problem

The inventors have surprisingly found that the dihydrofuranaone derivative of the formula (III) can be obtained without fear of fire and explosion by using a metal alkoxide and/or a metal hydroxide instead of sodium hydride in the above mentioned prior method.

Thus, the present invention relates to a process for preparing dihydrofurnanone derivative of the formula (III):

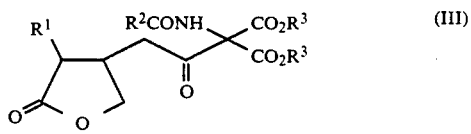

wherein $R^1$ and $R^3$ are individually lower alkyl, and $R^2$ is hydrogen or lower alkyl, by reacting a dihydrofuranone derivative of the formula (I):

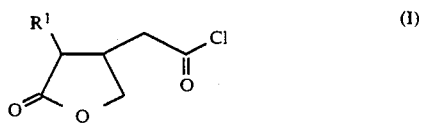

wherein $R^1$ is as defined above, with a malonic acid derivative of the formula (II):

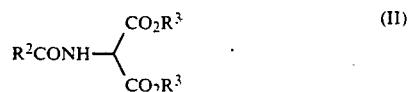

wherein $R^2$ and $R^3$ are as defined above, in the presence of an alkalimetal alkoxide and/or an alkalimetal hydroxide.

The starting compounds, dihydrofurnanone derivative (I) and malonic acid derivative (II), used in the present process, may be prepared in a way analogous to that described in the above reference.

The term "lower alkyl" in the definitions of $R^1$, $R^2$ and $R^3$ includes straight and branched chain alkyls, for example, methyl, ethyl, propyl, iso-propyl, n-butyl, sec-butyl, t-butyl, etc. The substituent $R^2$ denotes hydrogen atom in addition to lower alkyl.

The present process may be carried out usually in the presence of an inert solvent, for example, ethers such as diethyl ether, tetrahydrofuran, dioxane, 1,2-diethoxyethane, 1,2-dimethoxyethane; aromatic hydrocarbons such as benzene, toluene, xylene; amides such as formamide, dimethylformamide, N-methylpyrrolidone; etc. Tetrahydrofuran, toluene and dimethylformamide are preferred.

Examples of alkalimetal alkoxide are sodium methoxide, sodium ethoxide, sodium t-butoxide, potassium t-butoxide, and the like. Sodium ethoxide, sodium t-butoxide and potassium t-butoxide are preferred. As an alkalimetal hydroxide, sodium hydroxide, potassium hydroxide, lithium hydroxide, etc. may be used with sodium hydroxide and potassium hydroxide are preferred. The above mentioned compounds may be used alone or in combinations thereof. These compounds can be used safely due to lack of inflammability.

In the practice of the present invention, malonic acid derivative (II) is used in an amount of 0.1–5 mol, preferably 0.5–1.20 mol per mol of the starting compound dihydrofurnanone derivative (I), and alkalimetal alkoxide and/or alkalimetal hydroxide is used in an amount of 0.1–5 mol, preferably 0.5–1.2 mole per mole of the starting compound dihydrofuranone derivative (I). The amount of the solvent to be used in the range of about 2–100 times, preferably 5–30 times the weight of the starting compound dihydrofuranone derivative (I).

The reaction is conducted at $-30°$ C. to $+150°$ C., preferably at $3°$ C. to $+80°$ C. for 1 minute to 10 hours, preferably for 10 minutes to 5 hours. After completion of the reaction, the reaction mixture is worked up in a conventional way to give the desired product, dihydrofuranone derivative (III).

According to the present invention, there is provided, as mentioned above, a safe process for preparing dihydrofuranone derivatives of the formula (III).

EXAMPLE

The invention is further illustrated by the following Examples.

Though the following Examples refer to the preparation of the compound of the formula (III) wherein $R^1$ is ethyl, $R^2$ is methyl and $R^3$ is t-butyl, the present invention should in no way be construed as being limited to such compound only.

EXAMPLE 1

1.41 g (0.015 mol) of sodium t-butoxide and 10 ml of toluene were placed in 100 ml reactor equipped with a thermometer and a dropping funnel, and the mixture was stirred at room temperature for 30 minutes under $N_2$. To the mixture, a solution of 4.00 g (0.015 mol) of di-t-butyl acetamidomalonate in 30 ml of toluene was added dropwise at room temperature, followed by heating at $60°$ C. for 2 hours. The reaction mixture was cooled on ice, and a solution of the compound (I) ($R^1$ is ethyl, prepared from 2.52 g (0.015 mol) of (+)-homopilopic acid according to the method described in Tetrahedron 28: 967, 1972) in 10 ml of toluene was added wile maintaining the temperature below $10°$ C. After the addition, the reaction mixture was stirred for an additional hour.

To the mixture thus obtained, 20 ml of ice-water was added and the toluene layer was removed. Aqueous layer was extracted with 30 ml of ethyl acetate, and the combined organic layer was washed with saturated sodium chloride solution and dryed over anhydrous sodium sulfate. The organic layer was concentrated under reduced pressure to give an oil which was diluted with isopropyl alcohol to a volume of 100 ml. 5 ml aliquot of this solution was diluted with isopropyl alcohol to a volume of 25 ml. This solution was analyzed by HPLC column (column: R-SIL-5-06 S-5 60A, YMC, eluent: n-hexane/isopropyl alcohol 9:1, internal standard: 1-acetylaminoadamantane), and the yield of aimed dihydrofuranone derivative (III) was 70%. The remainder of the reaction mixture was purified by silicagel column chromatography (eluent: n-hexane/acetone 3:1), and the resultant solid was recrystallyzed from n-hexane/acetone 3:1 to give 3.77 g (yield 60%) of dihydrofurnanone derivative (III) wherein $R^1$ is ethyl, $R^2$ is methyl and $R^3$ is t-butyl as white crystals. The $^1$H-NMR and mass spectrum (molecular ion peak 428) of the crystals are identical with those of the authentic sample.

EXAMPLE 2

The procedure of Example 1 was followed using $(\pm)$-homopilopic acid instead of $(+)$-homopilopic acid.
Yield: 70% (HPLC).

EXAMPLE 3

The procedure of Example 1 was followed using 0.652 g (0.015 mol) of sodium hydroxide in 2 ml of $H_2O$ as a base, and a solution of di-t-butyl acetamidomalonate in the toluene which had previously been dehydrated by azeotropic distillation.
Yield: 49% (HPLC),

EXAMPLE 4

The procedure of Example 1 was followed using dioxane instead of toluene.
Yield: 51% (HPLC).

EXAMPLE 5

The procedure of Example 1 was followed using dimethylformamide instead of toluene.
Yield: 34% (HPLC).

EXAMPLE 6

The procedure of Example 1 was followed using 1.06 g of sodium ethoxide instead of sodium t-butoxide.
Yield: 42% (HPLC).

EXAMPLE 7

The procedure of Example 1 was followed using 1.06 g of sodium ethoxide instead of sodium t-butoxide and dry THF instead of toluene.
Yield: 62% (HPLC).

EXAMPLE 8

The procedure of Example 1 was followed except that 1.06 g of sodium ethoxide was used instead of sodium t-butoxide and the heating after the addition of the solution of di-t-butyl acetamidomalonate in toluene was effected at $90°$ C. instead of $60°$ C.
Yield: 32% (HPLC).

EXAMPLE 9

The procedure of Example 1 was followed using 1.06 g of sodium ethoxide instead of sodium t-butoxide and also using a solution of 4.00 g (0.015 mol) of di-t-butyl acetamidomalonate in 90 ml of toluene.
Yield: 18% (HPLC).

EXAMPLE 10

The procedure of Example 1 was followed using 1.06 g of sodium ethoxide instead of sodium t-butoxide and also using a solution of 4.00 g (0.015 mol) of di-t-butyl acetamidomalonate in 20 ml of toluene.
Yield: 32% (HPLC).

EXAMPLE 11

The procedure of Example 1 was followed using 1.74 g of potassium t-butoxide instead of sodium t-butoxide.
Yield: 49% (HPLC).

What is claimed is:
1. A process for preparing dihydrofuranone derivative of the formula (III):

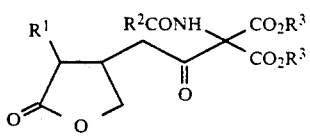

wherein $R^1$ and $R^3$ are individually lower alkyl, and $R^2$ is hydrogen or lower alkyl, by reacting a dihydrofuranone derivative of the formula (I):

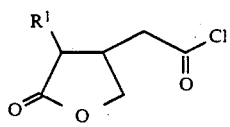

wherein $R^1$ is as defined above, with a malonic acid derivative of the formula (II):

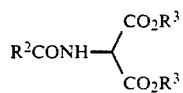

wherein $R^2$ and $R^3$ are as defined above, in the presence of an alkalimetal alkoxide and/or an alkalimetal hydroxide.

2. A process for producing a dihydrofuranone derivative of the formula (III):

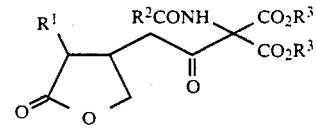

wherein $R^1$ is a lower alkyl, $R^2$ is hydrogen or a lower alkyl, and R3 is a lower alkyl, comprising reacting a dihydrofuranone derivative of the formula (I):

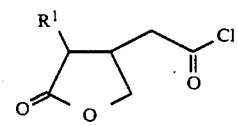

wherein $R^1$ is as defined above, with a malonic acid derivative of the formula (II):

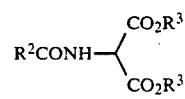

wherein $R^2$ and $R^3$ are as defined above, in a solvent in the presence of alkali metal alkoxide and/or alkali metal hydroxide, wherein said malonic acid derivative (II) is used in an amount of 0.5–1.2 mole per mole of said dihydrofuranone derivative (I), said alkali metal alkoxide and/or alkali metal hydroxide is used in an amount of 0.5–1.2 mole per mole of said dihydrofurnanone derivative (I), and the amount of said solvent is 5–30 times the weight of said dihydrofurnanone derivative (I).

* * * * *